United States Patent [19]
Sengupta et al.

[11] Patent Number: 5,900,511
[45] Date of Patent: May 4, 1999

[54] PROCESS FOR CONTINUOUS HYDROGENATION OF ADIPONITRILE

[75] Inventors: Sourav Kumar Sengupta; Theodore Augur Koch, both of Wilmington, Del.; Karl Robert Krause, Orange, Tex.

[73] Assignee: E. I. de Pont de Nemours and Company, Wilmington, Del.

[21] Appl. No.: 09/048,603

[22] Filed: Mar. 26, 1998

Related U.S. Application Data

[XX .
[60] Provisional application No. 60/042,126, Mar. 28, 1997.
[51] Int. Cl.$^6$ .................................................. C07C 209/48
[52] U.S. Cl. ............................................... 564/492
[58] Field of Search ............................... 564/492

[56] References Cited

U.S. PATENT DOCUMENTS 5,750,788  5/1998  Haussling et al. ...................... 564/415

*Primary Examiner*—Brian M. Burn

[57] ABSTRACT

A process for continuous hydrogenation of adiponitrile (ADN) to hexamethylene diamine (HMD) and optionally to amninocapronitrile (ACN) involving the catalytic hydrogenation of adiponitrile at relatively low temperature (e.g., 75° C.) and pressure (e.g., 500 psig) using a sponge cobalt catalyst (Raney® Co) in a reaction medium that is substantially free of caustic. In such a process periodic addition of water controls the production of side reaction products and the periodic addition of ammonium hydroxide rejuvenates the catalyst. Hexamethylene diamine is an important intermediate for the synthesis of polyamides such as Nylon-6,6 and aminocapronitrile is a potential intermediate of Nylon-6.

5 Claims, No Drawings

PROCESS FOR CONTINUOUS HYDROGENATION OF ADIPONITRILE

CROSS-REFERENCE TO RELATED APPLICATIONS

Applicants claim the benefit of priority to provisional application 60/042,126 filed Mar. 28, 1997.

BACKGROUND OF THE INVENTION

1. Field of the Invention

The present invention relates to an improved process for continuous hydrogenation of adiponitrile (ADN) to hexamethylene diamine (HMD) and aminocapronitrile (ACN). More specifically but not by way of limitation, the present invention relates to a process for the continuous hydrogenation of ADN at low temperature and pressure in the presence of a sponge cobalt catalyst and in a reaction medium substantially free of caustic.

2. Description of Related Art

It is generally known in the art that the hydrogenation of nitriles can be achieved by contacting a hydrogenation catalyst with a solution containing a nitrile, hydrogen, and an alkali or base. The reaction product typically contains primary amine as the desired product and one or more secondary and tertiary amines as adventitious side products. The secondary amines are believed to be formed by the reaction between primary amines and imine intermediates, formed by the partial hydrogenation of the primary amines. Tertiary amines, on the other hand, are the products of the reaction between secondary amines and additional imine intermediates. Various alternative methods for accomplishing such hydrogenation have been proposed including batch-processing in a stirred autoclave reactor, or by continuous processing, using a fixed-bed or bubble-flow reactor.

For example, in U.S. Pat. Nos. 3,758,584 and 3,773,832 a fixed-bed reactor has been used for the hydrogenation of ADN. HMD was prepared by hydrogenating ADN in packed bed reactors in the presence of excess of hydrogen and anhydrous ammonia, at temperatures of 85 to 185° C. and pressures of 4,000 to 6,000 psig. Cobalt or iron oxide was pelletized, calcined, and reduced in a mixture of hydrogen and ammonia at a temperature in the range of 300 to 600° C. The major drawbacks of this process are that it requires high temperature and pressure, a large amount of ammonia, reduction of iron or cobalt oxide catalyst used in this process, and difficulties associated with heat removal. Moreover, the cost of the catalyst used in the process has been increasing over time.

U.S. Pat. Nos. 4,429,159 and 4,491,673 describe the use of a Raney® nickel catalyst in a bubble-column reactor. The described process uses lower pressure (200 to 500 psig) and temperature (less than 100° C.). However, this process uses copious amounts of caustic to maintain the activity, selectivity, and the life of the catalyst. As a result, it requires expensive purification steps to produce high purity HMD.

A process for preparing HMD is disclosed in U.S. Pat. No. 5,105,015 where HMD is produced in a fixed bed reactor by hydrogenating ADN in the presence of granular Cr and Ni promoted Raney® Co catalyst. The reaction is carried out in the presence of at least 5 wt % ammonia (based on ADN) at a temperature and pressure in the range of 60 to 125° C. and 50 to 5,000 psi, respectively. The disadvantage of such a process is the inherent necessity to recover, purify, compress, and recycle ammonia (used as a solvent).

The preparation of a branched aliphatic diamine from the corresponding dinitrile is described in U.S. Pat. No. 4,885, 391. This patent discloses the hydrogenation of 2-methylglutaronitrile to 2-methyl, 1,5-pentamethylenediamine using chromium-promoted sponge cobalt catalyst in the presence of 0.5 to 4.0% by weight of water, at a temperature of about 80 to 150° C., and at a pressure of about 400 to 2,500 psig. While it is not obvious whether a branched aliphatic dinitrile will behave in the same fashion as a straight chain aliphatic dinitrile, it is apparent that the process makes a number of by-products including some cyclic condensation products. This would lead to a lower yield of the desired product during reaction, as well as separation. In addition, there would be a significant amount of water present that would need to be continuously pumped into the reaction vessel, to sustain the activity of the catalyst.

SUMMARY OF THE INVENTION

In view of the above it is an object of the present invention, to provide a low-temperature and low-pressure process for the continuous production of hexamethylene diamine and/or aminocapronitrile, by hydrogenating adiponitrile in the presence of a suitable sponge cobalt catalyst, substantially free of any inorganic base and/or water. It is a further object to provide a convenient way of regenerating the catalyst, in situ, and therefore, extend the effective life of the catalyst, a feature deemed necessary in a commercial process.

Thus the present invention provides an improved process for the continuous hydrogenation of adiponitrile to hexamethylene diamine and optionally to aminocapronitrile in a reaction medium which is substantially free of caustic comprising the steps of:

(i) contacting adiponitrile and hydrogen in the presence of a sponge cobalt catalyst and in a reaction medium which is substantially free of caustic at a temperature of 25 to 150° C. and at a pressure up to 2,000 psig for a time sufficient to convert at least a portion of said adiponitrile to hexamethylene diamine and optionally to aminocapronitrile;

(ii) continuously adding adiponitrile to the reaction medium;

(iii) continuously removing hexamethylene diamine and optionally aminocapronitrile from the reaction medium; and (iv) recovering the hexamethylene diamine and optionally the aminocapronitrile.

The above process according to the present invention further provides for controlling the production of side reaction products by the further steps of:

(i) adding water to the reaction medium when between 5 and 11 molar percent bishexamethylenetriamine (BHMT) appears in the reaction product, and (ii) discontinuing the water addition to the reaction medium when the level of BHMT in the reaction product drops below 1 molar percentage.

The process according to the present invention also provides for the rejuvenation of the catalyst, in situ, by the step of periodically adding an effective amount of ammonium hydroxide to the reaction medium.

DETAILED DESCRIPTION OF THE INVENTION

While the invention is felt to be generally applicable for the production of any straight-chain aliphatic polyamine and/or aminonitrile from a corresponding straight-chain aliphatic nitrile or polynitrile in which a sponge cobalt catalyst is employed, the invention will be described in the context of a preferred process for such production.

The present invention is also felt to be representative of a convenient, low-temperature, and low-pressure process for the continuous production of hexamethylene diamine and/or aminocapronitrile, by hydrogenating adiponitrile in the presence of a suitable sponge Co catalyst. As such the process may be of great use for the commercial production of hexamethylene diamine and/or aminocapronitrile.

As will be later illustrated in the examples, the process is typically initiated by contacting, preferably in a stirred or otherwise well-agitated autoclave reactor vessel, the desired product and hydrogen under pressure in the presence of a caustic solution followed by continuous addition of the reactant, such as adiponitrile, upon reaching the desired operating temperature. In this manner the continuous operation will ultimately be substantially free of caustic solution (also illustrated later in the examples). An important embodiment of the invention includes conducting the hydrogenation reaction substantially free of water and/or dilute caustic solution.

Preferably the catalyst is a finely-divided chromium and nickel modified ("chromium and nickel promoted") sponge cobalt. A "sponge metal" is one which has an extended porous "skeleton" or "sponge-like" structure of a metal, preferably a base metal (e.g. cobalt or nickel), with dissolved aluminum, optionally containing promoter(s). Sponge cobalt modified with at least one metal promoter of the group consisting of nickel, chromium, iron, and molybdenum are particular useful. The sponge metal catalysts also contain surface hydrous oxides, adsorbed hydrogen radicals, and hydrogen bubbles in the pores. Such catalysts are commercially available from W. R. Grace & Co. and Activated Metals, and contains about 0.5 to 6.0% by weight chromium and 0.5 to 6.0% by weight of nickel. Such catalysts, and the process for preparing them, are disclosed in EPO application No. 0,212,986.

The process of the present invention may be performed in a fixed bed (trickle-bed), or in a slurry phase using a sponge metal catalyst. When employing the process using a fixed bed catalyst, the catalyst is in the form of granules having a particle size in the range of about 0.03 to 0.40 inch. When employing the process using a slurry-phase catalyst, the catalyst is in finely-divided form, preferably less than about $100\mu$ in size, most preferred range being 20 to 75 $\mu$.

The ADN hydrogenation reaction can be carried out at a relatively low temperature ranging between 25 to 150° C., the preferred range of temperature being 50 to 125° C., and the most preferred range being 70 to 100° C. At lower temperatures, the rate of hydrogenation reaction becomes too slow, and the process of controlling the temperature of the exothermic reaction becomes too involved to be practical. On the other hand, higher temperatures usually induce the formation of undesired condensation products that end up as a waste, resulting in lower selectivity and yield of the desired product (hexamethylene diamine or aminocapronitrile).

The improved hydrogenation process of this invention may be performed at relatively low pressures. The currently practiced commercial method of hydrogenating adiponitrile, as described in U.S. Pat. Nos. 3,758,584 and 3,773,832, is carried out under high pressure and temperature, and requires a high investment. The advantage of using a low pressure process is that it lowers the investment cost of an industrial process. The instant hydrogenation reaction can proceed under pressures of hydrogen ranging from pressure sufficient to maintain acceptable flow of reactants and products necessary for the commercial production of the desired product(s) to pressures of less than 2000 psi (13.79 MPa). However, the preferred range of operating pressure is from 100 to 1,500 psi (0.69 MPa to 10.34 MPa), the most preferred range being 250 to 1000 psi (1.72 to 6.89 MPa).

A critical object of the present invention is to maximize the selectivity, and therefore, the yield of hexamethylene diamine or aminocapronitrile, at the highest possible conversion of the starting dinitrile. The yields of hexamethylene diamine and aminocapronitrile depend on operating conditions including temperature, pressure, hydrogen flow rate, amount and kind of catalyst, nature and concentration of solvent, presence and absence of added inorganic base, and space velocity, and the like. For the purpose of this invention, the term "space velocity" is defined as the unit weight of adiponitrile fed into the reactor per hour, per unit weight of the catalyst. Typically, adiponitrile should be added to the reactor such that the space velocity of adiponitrile is within the range of 0.5 to 5.0 when hexamethylene diamine and aminocapronitrile are the desired products, respectively. Most preferred space velocities for adiponitrile, those which maximize hexamethylene diamine and/or aminocapronitrile, may be readily determined by those skilled in the art using conventional techniques. When the rate of adiponitrile addition is below or above the herein stated space velocities, the selectivity and yield of the desired compound(s) diminish drastically, resulting in lower catalyst activity and shortened life of the catalyst.

The reactors useful for performing the continuous operation according to the instant invention include generally any conventional hydrogenation reactor. Examples of such reactors include, but are not limited to, plug flow reactor, continuous stirred tank reactor, and bubble column reactor. An example, of a bubble column reactor, which is not confined to this reaction, has been described in U.S. Pat. No. 4,429,159. Descriptions of plug flow and continuous stirred tank reactors have been delineated in the book entitled "Chemical Reaction Engineering" written by Octave Levenspiel.

Unless otherwise specified, the hydrogenation of adiponitrile illustrated in the following examples was carried out in a 300 cc autoclave designed and fabricated by Autoclave Engineers. The 300 cc reactor was constructed of Hastelloy-C with a maximum Allowable Working Pressure (MAWP) of ca 1500 psig at 300° C. The mixing in the reactor was performed with a magnetically coupled impeller, mounted on a hollow shaft and driven by an electric motor. The speed of the stirrer was monitored with a stroboscopic light. The reactor was heated with a 400 Watt external band heater.

The reactor was provided with a thermocouple insert, rupture disc, and two ⅛" dip legs fitted with 5 mm stainless steel frits, meant for liquid addition in to the reactor, and product withdrawal from the reactor respectively. Hydrogen was continuously fed in to the autoclave reactor via the hollow shaft of the agitator. The hydrogen flow rate in to the reactor was metered and monitored by a Brooks® mass flow controller. The pressure in the reactor was maintained with a Grove back pressure regulator. Adiponitrile was continuously fed to the reactor using an Isco syringe pump (260D series).

The reactor was connected to a 1 liter product receiver through a let-down tank. Samples were collected at the beginning of the experimental run and at specified time intervals (7 and 16 hours time intervals). The samples collected from the product receiver were melted and dissolved in isopropanol (solvent). Cyclododecane was added as an internal standard to the product sample and analyzed in a 5890A Hewlett-Packard capillary gas chromatograph.

It should be appreciated that the following examples are presented to more fully demonstrate and further illustrate various individual aspects and features of the present invention and as such the examples are felt to be non-limiting and are meant to illustrate the invention but are not meant to be unduly limiting in any way.

EXAMPLE 1

HMD Synthesis in the Absence of Water and Caustic

120 Grams of HMD, 0.6 ml caustic solution (50% sodium hydroxide), and 15 grams (7.5 g of dry catalyst in 7.5 g water) of preactivated Raney® cobalt catalyst (W. R. Grace 2724) were loaded in the reactor. The autoclave was sealed, flushed with nitrogen several times and pressure tested at 500 psig. After ensuring that there were no leaks, the reactor was heated to 75° C. and the agitator switched on (1200 rpm). As soon as the desired reaction temperature was achieved, the reactor pressure was set to 500 psig by adjusting the back pressure regulator, and the hydrogen flow rate was set to 600 sccm. ADN was then continuously added to the reactor at the rate of 12 grams per hour. The hold up time of the product(s) in the reactor was 10 hours. The production of HMD and the product distribution as a function of time on stream as well as the grams ADN fed per gram of catalyst are presented in Table 1. The presence of caustic (sodium associated with the starting NaOH) was not detected by Inductively Coupled Plasma (ICP) analysis after 48 hours of time on stream. Also, aqueous ammonium hydroxide solution was added after 816 hours and stopped at 888 hours and again started after 1035 hours and continued until the end of the experimental run. The purpose of the addition of ammonium hydroxide was to demonstrate in situ rejuvenation of the catalyst.

TABLE 1

| Time on Stream (hr) | gm ADN Fed/ gm of Catalyst | HMD Produced (gm) | Product Distribution | | | |
|---|---|---|---|---|---|---|
| | | | HMD (%) | ACN (%) | ADN (%) | BHMT (%) |
| 0.0 | 0.0 | 0.0 | 100.0 | 0.0 | 0.0 | 0.0 |
| 24.0 | 37.2 | 269.7 | 99.4 | 0.0 | 0.0 | 0.4 |
| 72.0 | 111.5 | 809.4 | 97.2 | 0.0 | 2.3 | 0.3 |
| 120.0 | 185.8 | 1362.2 | 99.7 | 0.0 | 0.0 | 0.3 |
| 168.0 | 260.1 | 1913.0 | 98.0 | 0.0 | 0.0 | 0.3 |
| 216.0 | 334.4 | 2464.4 | 98.7 | 0.0 | 0.8 | 0.5 |
| 240.0 | 371.6 | 2739.6 | 98.6 | 0.0 | 0.0 | 1.2 |
| 288.0 | 445.9 | 3292.6 | 99.2 | 0.0 | 0.0 | 0.6 |
| 336.0 | 520.2 | 3843.8 | 99.3 | 0.0 | 0.0 | 0.5 |
| 384.0 | 594.5 | 4384.9 | 95.4 | 0.0 | 2.9 | 1.5 |
| 432.0 | 668.8 | 4932.2 | 97.7 | 0.0 | 0.0 | 2.3 |
| 480.0 | 743.1 | 5473.2 | 97.9 | 0.0 | 0.0 | 2.1 |
| 528.0 | 817.4 | 6016.3 | 97.2 | 0.0 | 0.0 | 2.6 |
| 576.0 | 891.7 | 6557.8 | 96.9 | 0.0 | 0.0 | 2.9 |
| 624.0 | 966.1 | 7098.6 | 97.5 | 0.0 | 0.0 | 2.3 |
| 672.0 | 1040.4 | 7627.1 | 93.1 | 0.0 | 0.0 | 5.5 |
| 720.0 | 1114.7 | 8148.7 | 93.6 | 0.0 | 0.0 | 6.4 |
| 768.0 | 1189.0 | 8668.1 | 93.1 | 0.0 | 0.0 | 6.9 |
| 816.0 | 1263.3 | 9188.4 | 93.6 | 0.0 | 0.0 | 6.4 |
| 864.0 | 1337.6 | 9719.8 | 96.1 | 0.0 | 0.0 | 3.9 |
| 888.0 | 1374.8 | 9988.2 | 96.3 | 0.0 | 0.0 | 3.7 |
| 941.0 | 1456.8 | 10577.4 | 95.3 | 0.0 | 0.0 | 4.7 |
| 987.0 | 1528.0 | 11087.4 | 94.7 | 0.0 | 0.0 | 5.3 |
| 1035.0 | 1602.3 | 11615.3 | 94.5 | 0.0 | 0.0 | 5.5 |
| 1083.0 | 1676.7 | 12160.2 | 97.6 | 0.0 | 0.0 | 2.4 |
| 1131.0 | 1751.0 | 12703.2 | 97.6 | 0.0 | 0.0 | 2.4 |
| 1179.0 | 1825.3 | 13242.5 | 97.0 | 0.0 | 0.0 | 2.1 |

Comparative Example

The experimental run of Example 1 was repeated except 120 grams of methylpentamethylenediamine (MPMD) (desired product) was used instead of HMD and the reaction was carried out at 130° C. instead of 75° C. The results indicated that the reaction of methylglutaronitrile (MGN) under the above operating conditions primarily produced undesirable side products. The resulting data are presented in Table A.

TABLE A

| Time on Stream (hr) | gm MGN Fed/ gm of Catalyst | HMD MPMD (%) | Product Distribution | | | |
|---|---|---|---|---|---|---|
| | | | *3MePip (%) | C6-Amine (%) | MGN (%) | others (%) |
| 0.0 | 0.0 | 100.0 | 0.0 | 0.0 | 0.0 | 0.0 |
| 24.0 | 37.2 | 3.6 | 65.5 | 14.0 | 1.40 | 15.5 |
| 48.0 | 74.4 | 20.1 | 44.6 | 12.8 | 0.4 | 22.1 |
| 72.0 | 111.5 | 12.2 | 60.9 | 11.6 | 1.1 | 14.2 |

TABLE A-continued

| Time on Stream (hr) | gm MGN Fed/ gm of Catalyst | HMD MPMD (%) | *3MePip (%) | C6-Amine (%) | MGN (%) | others (%) |
|---|---|---|---|---|---|---|
| 96.0 | 148.8 | 6.4 | 70.0 | 10.2 | 1.7 | 11.7 |
| 120.0 | 185.8 | 10.9 | 60.8 | 9.5 | 0.9 | 17.9 |

*3-methylpiperidone

EXAMPLE 2

In a manner analogous to that of Example 1 a second run was performed at essential identical conditions except water was added continuously to the reactor at the rate of 0.6 ml per hour. The resulting data are presented in Table 2.

TABLE 2

| Time on Stream (hr) | gm ADN Fed/ gm of Catalyst | HMD Produced (gm) | HMD (%) | ACN (%) | ADN (%) | BHMT (%) |
|---|---|---|---|---|---|---|
| 0.0 | 0.0 | 0.0 | 100.0 | 0.0 | 0.0 | 0.0 |
| 24.0 | 37.2 | 278.7 | 100.0 | 0.0 | 0.0 | 0.0 |
| 48.5 | 75.1 | 563.1 | 100.0 | 0.0 | 0.0 | 0.0 |
| 91.0 | 140.9 | 1056.6 | 100.0 | 0.0 | 0.0 | 0.0 |
| 120.7 | 186.8 | 1401.1 | 100.0 | 0.0 | 0.0 | 0.0 |
| 145.0 | 224.5 | 1683.6 | 100.0 | 0.0 | 0.0 | 0.0 |
| 169.0 | 261.6 | 1962.3 | 100.0 | 0.0 | 0.0 | 0.0 |
| 190.0 | 294.2 | 2206.1 | 100.0 | 0.0 | 0.0 | 0.0 |
| 219.0 | 339.0 | 2536.8 | 97.7 | 0.0 | 0.0 | 2.3 |
| 258.7 | 400.5 | 2993.0 | 98.2 | 0.0 | 0.0 | 1.8 |
| 284.0 | 439.7 | 3280.2 | 97.2 | 0.0 | 0.0 | 2.8 |
| 308.0 | 476.8 | 3551.9 | 98.0 | 0.0 | 0.0 | 2.0 |
| 331.0 | 512.4 | 3807.4 | 97.1 | 0.0 | 0.0 | 2.9 |
| 354.0 | 548.0 | 4062.9 | 96.3 | 0.0 | 0.0 | 3.7 |
| 377.0 | 583.7 | 4318.I | 96.4 | 0.0 | 0.0 | 3.6 |
| 418.0 | 647.1 | 4772.5 | 95.2 | 0.0 | 0.0 | 4.5 |
| 448.0 | 693.6 | 5104.5 | 95.5 | 0.0 | 0.0 | 4.5 |
| 471.0 | 729.2 | 5356.3 | 94.2 | 0.0 | 0.0 | 5.8 |
| 494.0 | 764.8 | 5604.0 | 93.7 | 0.0 | 0.0 | 6.3 |
| 517.0 | 800.4 | 5852.6 | 93.0 | 0.0 | 0.0 | 7.0 |
| 540.0 | 836.0 | 6098.6 | 92.1 | 0.0 | 0.0 | 7.9 |
| 584.0 | 904.1 | 6567.5 | 91.7 | 0.0 | 0.0 | 8.3 |
| 607.0 | 939.7 | 6809.0 | 90.4 | 0.0 | 0.0 | 9.6 |
| 630.0 | 975.3 | 7043.1 | 87.3 | 0.0 | 0.0 | 11.5 |
| 653.0 | 1010.9 | 7274.4 | 86.4 | 0.0 | 0.0 | 12.5 |
| 680.0 | 1052.7 | 7537.7 | 85.2 | 0.0 | 0.0 | 13.4 |
| 702.0 | 1086.8 | 7743.8 | 70.1 | 13.4 | 7.7 | 5.5 |

EXAMPLE 3
Effect of the Addition of Dilute Caustic Solution

Again in a manner analogous to that of Example 1 a third run was performed at essentially identical conditions except 1 wt % aqueous caustic solution was added continuously to the reactor at the rate of 0.6 ml per hour. The resulting data are presented in Table 3.

TABLE 3

| Time on Stream (hr) | gm ADN Fed/ gm of Catalyst | HMD Produced (gm) | HMD (%) | ACN (%) | ADN (%) | BHMT (%) |
|---|---|---|---|---|---|---|
| 0.0 | 0.0 | 0.0 | 100.0 | 0.0 | 0.0 | 0.0 |
| 20.0 | 31.0 | 230.8 | 99.6 | 0.0 | 0.0 | 0.4 |
| 68.0 | 105.3 | 782.4 | 98.7 | 0.0 | 0.0 | 1.3 |
| 117.0 | 181.1 | 1341.2 | 97.9 | 0.0 | 0.0 | 2.1 |
| 164.0 | 253.9 | 1872.1 | 96.8 | 0.0 | 0.0 | 3.2 |
| 210.0 | 325.1 | 2384.2 | 95.5 | 0.0 | 0.0 | 4.5 |

TABLE 3-continued

| Time on Stream (hr) | gm ADN Fed/ gm of Catalyst | HMD Produced (gm) | Product Distribution | | | |
|---|---|---|---|---|---|---|
| | | | HMD (%) | ACN (%) | ADN (%) | BHMT (%) |
| 248.0 | 383.9 | 2799.3 | 92.8 | 0.0 | 1.9 | 5.3 |
| 296.0 | 458.3 | 3324.0 | 94.2 | 0.0 | 0.0 | 5.8 |
| 344.0 | 532.6 | 3829.9 | 90.5 | 0.0 | 2.4 | 7.0 |
| 392.0 | 606.9 | 4345.8 | 91.8 | 0.0 | 1.0 | 7.1 |
| 446.0 | 690.5 | 4932.6 | 93.3 | 1.6 | 0.3 | 4.8 |
| 494.0 | 764.8 | 5440.4 | 90.0 | 4.1 | 2.7 | 3.2 |
| 542.0 | 839.1 | 5924.2 | 84.3 | 8.9 | 4.1 | 2.7 |
| 590.0 | 913.4 | 6346.4 | 75.5 | 14.9 | 7.0 | 2.5 |
| 641.0 | 992.4 | 6740.7 | 59.1 | 21.6 | 17.0 | 2.3 |
| 685.0 | 1060.5 | 6934.5 | 30.3 | 25.2 | 43.4 | 1.1 |
| 757.0 | 1172.0 | 7114.5 | 19.5 | 21.5 | 58.8 | 0.2 |

EXAMPLE 4
Selective Synthesis of Aminocapronitrile

A fourth run was performed in a manner analogous to Example 1, except the reaction was carried out in a 500 cc autoclave and 200 grams of HMD, 0.6 ml caustic solution (50 wt % sodium hydroxide), and 10 grams (5.0 g of dry catalyst in 5.0 g water) of preactivated Raney® cobalt (Grace 2724) were loaded in the reactor. The feed rate of ADN was maintained at 18 grams per hour at a hold up time of 11.1 hours. The resulting data are presented in Table 4.

TABLE 4

| Time on Stream (hr) | gm ADN Fed/ gm of Catalyst | HMD (%) | Product Distribution | | BHMT (%) |
|---|---|---|---|---|---|
| | | | ACN (%) | ADN (%) | |
| 0.0 | 0.0 | 100.0 | 0.0 | 0.0 | 0.0 |
| 2.3 | 7.8 | 100.0 | 0.0 | 0.0 | 0.0 |
| 9.3 | 32.2 | 95.9 | 0.0 | 0.0 | 4.1 |
| 18.3 | 63.6 | 98.6 | 0.0 | 0.0 | 0.0 |
| 26.3 | 91.4 | 58.9 | 16.2 | 23.6 | 0.0 |
| 42.3 | 175.0 | 49.5 | 26.9 | 21.3 | 0.0 |
| 50.0 | 174.2 | 53.1 | 24.2 | 19.0 | 0.0 |
| 66.8 | 232.5 | 43.7 | 24.5 | 28.5 | 0.0 |
| 74.3 | 258.6 | 29.6 | 25.8 | 42.0 | 0.0 |
| 90.8 | 316.1 | 35.0 | 25.2 | 36.9 | 0.0 |
| 95.3 | 331.8 | 26.3 | 25.3 | 46.1 | 0.0 |

Having thus described and exemplified the invention with a certain degree of particularity, it should be appreciated that the following claims are not to be so limited but are to be afforded a scope commensurate with the wording of each element of the claim and equivalents thereof.

We claim:

1. A process for the continuous hydrogenation of adiponitrile to hexamethylene diamine and optionally to aminocapronitrile in a reaction medium which is substantially free of caustic comprising the steps of:

(i) contacting adiponitrile and hydrogen in the presence of a sponge cobalt catalyst and in a reaction medium which is substantially free of caustic at a temperature of 25 to 150° C. and at a pressure up to 2,000 psig for a time sufficient to convert at least a portion of said adiponitrile to hexamethylene diamine and optionally to aminocapronitrile;

(ii) continuously adding adiponitrile to said reaction medium;

(iii) continuously removing hexamethylene diamine and optionally aminocapronitrile from said reaction medium; and (iv) recovering said hexamethylene diamine and optionally said aminocapronitrile.

2. The process of claim 1 further comprising:

(i) adding water to the reaction medium when between 5 and 11 molar percent BHMT appears in the reaction product, and (ii) discontinuing the water addition to the reaction medium when the level of BHMT in the reaction product drops below 1 molar percentage.

3. The process of claim 1 wherein the amount of adiponitrile supplied to the reaction medium is from 0.5 to 5.0 grams/hour per gram of catalyst.

4. The process of claim 3 where the sponge cobalt is modified with 0.5 to 6.0 weight % of at least one of the group consisting of nickel, chromium, iron, and molybdenum.

5. The process of claim 1 further comprising the step of periodically adding an effective amount of ammonium hydroxide to said reaction medium to rejuvenate said catalyst.

* * * * *